(12) United States Patent
Shimamoto et al.

(10) Patent No.: US 7,622,499 B2
(45) Date of Patent: Nov. 24, 2009

(54) β-BENZYLOXYASPARTATE DERIVATIVES WITH PHOTOSENSITIVE GROUPS (75) Inventors: Keiko Shimamoto, Suita (JP); Kiyo Takaoka, Takatsuki (JP)

(73) Assignee: Suntory Holdings Limited, Osaka (JP)

( * ) Notice: Subject to any disclaimer, the term of this patent is extended or adjusted under 35 U.S.C. 154(b) by 484 days.

(21) Appl. No.: 10/558,374

(22) PCT Filed: May 30, 2003

(86) PCT No.: PCT/JP03/06876

§ 371 (c)(1),
(2), (4) Date: Dec. 22, 2006

(87) PCT Pub. No.: WO2004/106286

PCT Pub. Date: Dec. 9, 2004

(65) Prior Publication Data
US 2007/0158175 A1 Jul. 12, 2007

(51) Int. Cl.
A61K 31/352 (2006.01)
C07D 311/04 (2006.01)

(52) U.S. Cl. .............. 514/456; 549/200; 549/356; 549/399; 562/400; 562/443; 562/568; 514/451; 514/453; 514/567

(58) Field of Classification Search .......... 549/200, 549/356, 381, 396, 399; 562/400, 443, 512, 562/568; 514/451, 453, 456, 561, 567
See application file for complete search history.

(56) References Cited

U.S. PATENT DOCUMENTS 6,147,113 A * 11/2000 Shimamoto et al. ......... 514/533
7,247,652 B2 * 7/2007 Shimamoto ................. 514/533

FOREIGN PATENT DOCUMENTS

EP 0 844 234 B1 3/2002
WO WO 00/31588 6/2000

OTHER PUBLICATIONS

Wilcox et al., "Synthesis of Photolabile 'Precursors' of Amino Acid Neurotransmitters," J. Org. Chem., 1990, vol. 55, pp. 1585-1589, American Chemical Society, Columbus, OH.

Weiboldt et al., "Photolabile precursors of glutamate: Synthesis, photochemical properties, and activation of glutamate receptors on a microsecond time scale," Proc. Natl. Acad. Sci. USA, Sep. 1994, vol. 91, pp. 8752-8756, National Academy of Sciences, Washington, DC.

Eckardt et al., "Deactivation Behavior and Excited-State Properties of (Coumarin-4-yl)methyl Derivatives. 2. Photocleavage of Selected (Coumarin-4-yl)methyl-Caged Adenosine Cyclic 3',5'-Monophosphates with Fluorescence Enhancement," J. Org. Chem., 2002, vol. 67, pp. 703-710, American Chemical Society, Columbus, OH.

Hagen et al., "Highly Efficient and Ultrafast Phototriggers for cAMP and cGMP by Using Long-Wavelength UV/Vis-Activation," Angew. Chem. Int. Ed., 2001, vol. 40, No. 6, pp. 1046-1048.

(Continued)

Primary Examiner—Golam M Shameem
(74) Attorney, Agent, or Firm—Drinker Biddle & Reath LLP (57) ABSTRACT

The present invention relates to photosensitive derivatives of optically active L-threo-β-benzyloxyaspartate or its benzene ring-substituted analogs, represented by the following formula (1) or (2): (1) (2) wherein $R^1$ represents hydrogen atom, amino group, straight or branched lower aliphatic acylamino group optionally substituted at the acyl group portion, alicyclic acylamino group or aromatic acylamino group optionally having a substituent on the aromatic ring, $R^2$ represents hydrogen atom or one or more straight or branched optionally substituted lower aliphatic alkyloxy groups on the benzene ring, R3 represents hydrogen atom, methyl group or carboxyl group, and R4 and R5 each represent hydrogen atom, hydroxyl group, straight or branched lower alkyloxy group optionally substituted at the alkyl portion, amino group, straight or branched lower alkyl-substituted amino group, or a halogen atom, which upon photoirradiation can produce compounds exhibiting a function of suppressing the glutamate uptake activity of L-glutamate transporters.

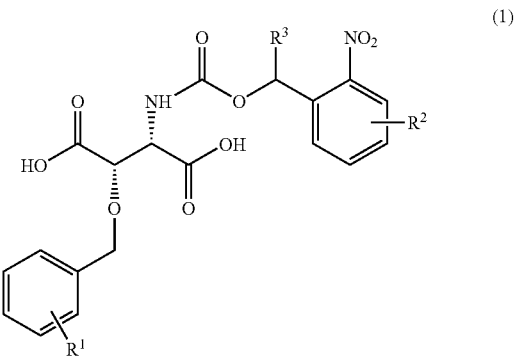

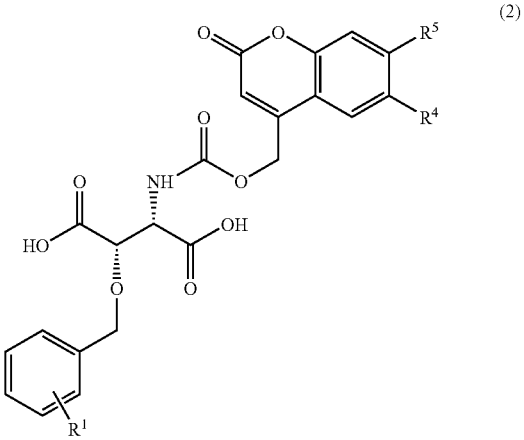

6 Claims, 3 Drawing Sheets

OTHER PUBLICATIONS

Furuta et al., "Brominated 7-hydroxycoumarin-4-ylmethyls: Photolabile protecting groups with biologically useful cross-sections for two photon photolysis," Proc. Natl. Acad. Sci. USA, Feb. 1999, vol. 96, pp. 1193-1200, National Academy of Sciences, Washington, DC.

Takaoka et al., "Synthesis and Photoreactivity of Caged Blockers for Glutamate Transporters," Bioorganic & Medicinal Chemistry Letters, vol. 13, 2003, pp. 965-970.

Shimamoto et al., "DL-threo-β-Benzyloxyaspartate, a Potent Blocker of Excitatory Amino Acid Transporters," Molecular Pharmacology, vol. 53, pp. 195-201, 1998, American Society for Pharmacology & Experimental Therapeutics, Baltimore, MD.

Rossi et al., "N-Nmoc-L-Glutamate, a New Caged Glutamate with High Chemical Stability and Low Pre-photolysis Activity," The Journal of Biological Chemistry, vol. 272, No. 52 Dec. 26, 1997, pp. 32933-32939, American Society for Biochemistry and Molecular Biology, Baltimore, MD.

International Search Report dated Jan. 8, 2004 for International PCT No. PCT/JP03/06876.

* cited by examiner

β-BENZYLOXYASPARTATE DERIVATIVES WITH PHOTOSENSITIVE GROUPS

TECHNICAL FIELD OF THE INVENTION

The present invention relates to L-glutamate uptake inhibition, and more specifically it relates to photosensitive derivatives of optically active L-threo-β-benzyloxyaspartate or its benzene ring-substituted analogs represented by the following formula (1):

Formula (1)

wherein $R^1$ represents hydrogen atom, amino group, straight or branched lower aliphatic acylamino group optionally substituted at the acyl group portion, alicyclic acylamino group or aromatic acylamino group optionally having a substituent on the aromatic ring, $R^2$ represents hydrogen atom or one or more straight or branched optionally substituted lower aliphatic alkyloxy groups on the benzene ring, and $R^3$ represents hydrogen atom, methyl group or carboxyl group, or formula (2):

Formula (2)

wherein $R^1$ is the same as $R^1$ in formula (1), and $R^4$ and $R^5$ each represent hydrogen atom, hydroxyl group, straight or branched lower alkyloxy group optionally substituted at the alkyl portion, amino group, straight or branched lower alkyl-substituted amino group, or a halogen atom, which upon photoirradiation can produce compounds exhibiting a function of suppressing the glutamate uptake activity of L-glutamate transporters.

These compounds can be used to search for clues toward elucidating the mechanism of glutamate uptake by L-glutamate transporters, and are therefore expected to greatly advance the development of treatments for neurological disorders and neurodegenerative conditions such as epilepsy, Huntington's disease, amyotrophic lateral sclerosis (ALS) and Alzheimer's disease.

PRIOR ART

L-glutamate is an excitatory neurotransmitter of the mammalian central nervous system, which is known to cause rapid neural transmission between synapses, while also being involved in the higher complex physiological processes of memory and learning. Excitatory neurotransmission between synapses begins with release of glutamate from the presynapse, and subsides by rapid glutamate uptake from the synaptic cleft by high-affinity glutamate transporters present in nerve endings and glia cells (Attwell, D. and Nicholls, D., TIPS 68-74, 1991; Danbolt, N. C. Prog. Neurobiol. 65, 1-105, 2001).

Reduced sodium-dependent glutamate uptake activity has been reported in certain parts of the brain of some inherited neurodegenerative patients (Rothstein, J. D. et al., N. Eng. J. Med. 326, 1464-1468, 1992). Expression and inhibition of glutamate transporter function have therefore been drawing attention in connection with these diseases. Molecular biological research in this area began with cloning of sodium-dependent high-affinity glutamate transporter cDNA in 1992 (Pines, G. et al., Nature 360, 464-467, 1992; Storck, T. et al., Proc. Natl. Acad. Sci. USA, 89, 10955-10959, 1992; Kanai, Y. et al., Nature 360, 467-471, 1992). In 1994, a human glutamate transporter gene was also cloned and was classified as subtype EAAT1-5 (Arriza, J. L. et al., J. Neurosci. 14, 5559-5569; Fairman, W. A. et al., nature, 375, 599-603, 1995; Arriza, J. L. et al., Proc. Natl. Acad. Sci. USA 94, 4155-4160, 1997).

The physiological roles of transporters have in several cases been investigated by analysis using knockout mice (Rothstein, J. D. et al., Neuron, 16, 675-686, 1996; Tanaka, K. et al., Science, 276, 1699-1702, 1997). However, although knockout mice permit the study of chronic functional deficiency, they are not suitable for examining the effects of acute transporter deficiency, while such research has also been limited by the fact that a deficiency in one type of transporter is often compensated for by the function of another transporter. For this reason, medical inhibition of transporters has been indispensable in elucidating their physiological roles.

The present inventors have previously reported that β-hydroxyaspartate derivatives with substituents at the β carbon exhibit uptake inhibition for all EAAT1-5 subtypes (Lebrun, B. et al., J. Biol. Chem. 272, 20336-20339, 1997; Shimamoto, K. et al., Mol. Pharmacol. 53, 195-201, 1998; Shigeri, Y. et al., J. Neurochem. 79, 297-302, 2001). It has been found that compounds with bulky substituents at the β carbon act as blockers for all subtypes, and inhibit not only glutamate uptake but also heteroexchange-type glutamate leakage and sodium ion influx (Chatton, J-Y. et al., Brain Res. 893, 46-52, 2001). Particularly powerful blocker activity is exhibited by L-threo-β-benzyloxyaspartate (L-TBOA), and because of its lower affinity for glutamate receptor compared to existing inhibitors, it has become a standard substance used for glutamate transporter research.

The present inventors have also examined the structure-activity relationship based on the structure of TBOA, and have discovered that compounds having substituents on the benzene ring of TBOA, and especially 3-(4-trifluoromethylbenzoyl)amino derivative (TFB-TBOA) and 3-(4-methoxybenzoyl)amino derivative (PMB-TBOA), exhibit more powerful inhibitory activity than L-TBOA (Japanese Patent Application No. PCT-JP02-06286).

SUMMARY OF THE INVENTION

For more detailed elucidation of the substrate transport mechanism and physiological role of a glutamate transporter it is necessary to inhibit the transporter under temporally and positionally limited conditions. However, control of the conditions, such as cell-specific drug administration or drastic drug concentration increase, has been difficult to achieve using conventional methods of drug administration.

DETAILED DESCRIPTION OF THE INVENTION

In recent years, it has become possible to suppress the activity of physiologically active substances by protecting their active sites with photosensitive groups and to regenerate their activity by deprotection with photoirradiation when necessary. Such substances are known as "caged compounds". Development of this technology, with discretionary timing of photoirradiation, has made it possible to produce drastic increases in drug concentration during desired periods. Using laser beam as the light source permits photoirradiation of only specific cells to stimulate only them and their immediate vicinity. Caged glutamate has been developed, for example (Wilcox, M et al, J. Org. Chem., 55, 1585-1589, 1990; Furuta, T. et al., Proc. Natl. Acad. Sci. USA, 96, 1193-1200, 1999; Tsien, R. and Furuta, T. PCT-US99-27591, 1999). As concerns glutamate transporter-related reagents, success has been reported in instantaneously increasing the concentration of its agonist D-aspartate thereby resulting in transporter activation (Grewer, C. et al., Biochemistry, 40, 232-240, 200), but instantaneous inactivation of a transporter has not yet been achieved.

On the assumption that application of caging technology to transporter inhibitors would allow positionally and temporally selective inhibition, we synthesized compounds having photosensitive groups introduced therein in ester form, similar to caged glutamate. Photosensitive protecting groups which have been found to be effective include nitrobenzyl-type protecting groups which are commonly used as caging groups (Wilcox, M et al, J. Org. Chem., 55, 1585-1589, 1990; Wieboldt, R. et al., Proc. Natl. Acad. Sci. USA. 91, 8752, 1994; for review Gee, K. R. et al., Methods in enzymology, 291, 30-50, 1998), as well as coumarylmethyl-type protecting groups (Eckardt, T. et al., J. Org. Chem., 67, 703-710, 2002; Hagen, V. et al., Angew. Chem. Int. Ed., 40, 1045-1048, 2001; Furuta, T. et al., J. Org. Chem., 60, 3953-3956, 1995; Furuta, T. et al., Proc. Natl. Acad. Sci. USA, 96, 1193-1200, 1999; Tsien, R. and Furuta, T., PCT WO 00/31588). TBOA derivatives having coumarylmethyl-type protecting groups exhibited particularly high photosensitivity compared to nitrobenzyl-type protecting groups (Takaoka, K. et al., Bioorganic & Medicinal Chemistry Letters, 13, 965-970, 2003). However, although compounds having photosensitive groups as an ester form have high photosensitivity, their tendency to gradually decompose in aqueous solution has constituted an impediment to their practical use. As a result of persistent investigation by selection of different photosensitive protecting groups and binding positions, it was found that introduction of a photosensitive group as a carbamate at the α-amino group of TBOA or benzoylamido-substituted TBOA can preserve the stability of the molecule in aqueous solution. The photosensitivity of the resulting carbamate-type compound was lower than the ester form, but by introduction of the appropriate substituent on the photosensitive protecting group it was possible to improve the reactivity to a high level comparable to that of the ester-type compound. The caged glutamate transporter inhibitors obtained according to the invention exhibited less than 1/300 of their original inhibitory activity prior to photoirradiation, but recovered their activity upon photoirradiation, and the present invention was thereupon completed.

In other words, the present invention provides caged blockers for glutamate transporters, whose activity expression can be controlled by UV light, which are nitrobenzyl-type photosensitive compounds and coumarin-type photosensitive compounds represented by chemical formulas (1) and (2) above and their salts, having photosensitive protecting groups on the α-amino group of optically active β-benzyloxyaspartate or its benzene ring-substituted analogs.

The optically active β-benzyloxyaspartate and its benzene ring-substituted analogs are compounds represented by formula (3) below, wherein $R^1$ is hydrogen, amino, straight or branched lower aliphatic acylamino optionally substituted at the acyl group portion, alicyclic acylamino or aromatic acylamino optionally having a substituent on the aromatic ring.

The acyl group portion in these groups can be of $C_1$-$C_6$ carbon chain length, and examples of acyl groups of the straight or branched or alicyclic acylamino groups as $R^1$ include acetyl, propionyl, n-butanoyl, sec-butanoyl, n-pentanoyl, pivaloyl and cyclohexylcarbonyl. The acyl groups may also have substituents such as amino, hydroxyl or biotinyl group. Examples of aromatic acyl groups of the aromatic acylamino groups as $R^1$ include benzoyl, naphthoyl and pyridylcarbonyl. The aromatic rings may also have substituents. Examples of substituents on the aromatic rings include straight or branched alkyl, aryl, alkoxyl, nitro, cyano, amino, acylamino, carboxyl, halogens, halogenated alkyl, biotinyl and biotinylalkyl.

Formula (3)

The nitrobenzyl-type photosensitive compounds are represented by general formula (1), and are compounds with an o-nitrobenzyl derivative substitution by a carbamate bond at the α-amino group of compounds represented by formula (3). In formula (1), $R^1$ is equivalent to $R^1$ in formula (3), and $R^2$ represents hydrogen or straight or branched lower aliphatic $C_1$-$C_6$ alkyloxy, of which optionally two or more may be substituted on the nitrobenzene ring. $R^3$ represents hydrogen, methyl or carboxyl.

The coumarin-type photosensitive compounds are represented by general formula (2), and are compounds substituted by coumarylmethyl derivatives as a carbamate at the α-amino group of compounds represented by formula (3). In formula (2), $R^1$ is equivalent to $R^1$ in formula (3), and $R^4$ and $R^5$ each represent hydrogen, hydroxyl, straight or branched $C_1$-$C_6$ lower alkyloxy optionally substituted at the alkyl portion, amino, straight or branched lower alkyl-substituted amino, or a halogen. As examples of straight or branched alkyl groups there may be mentioned methyl, ethyl, n-propyl, iso-propyl, n-butyl and t-butyl, and substituents for the alkyl groups include carboxyl, amino, halogens and thiol.

The compounds of the invention may be converted to salts by conventional methods. Such salts include alkali metal salts such as sodium and potassium salts, alkaline earth metal salts such as calcium salts, or ammonium salts and the like, and all such salts are included in the invention.

The compounds of the invention may be synthesized in the following manner. For example, the following is a synthesis pathway for a compound of formula (2) wherein $R^1$ is hydrogen, $R^4$ is hydrogen and $R^5$ is carboxymethoxy (N-CMCMC-TBOA: 5a) and a compound of formula (2) wherein $R^1$ is hydrogen, and $R^4$ and $R^5$ are both carboxymethoxy (N-BCMCMC-TBOA: 5b) (Scheme 1). Specifically, a protected TBOA (1) is partially deprotected to obtain compound 2 possessing the free α-amino group, and this is reacted with a chloroformate (3a or 3b) prepared from the corresponding alcohol and phosgene to obtain a protected carbamate (4). After deprotection with a strong acid such as TFA, it is purified by high-performance liquid chromatography to obtain the target compound (5a or 5b).

The following is a synthesis pathway for a compound of formula (2) wherein $R^1$ is 3-(4-trifluoromethylbenozyl)amino and $R^4$ and $R^5$ are both carboxymethoxy (N-BCM- CMC-TFB-TBOA: 9) (Scheme 2). Specifically, the target compound (9) may be obtained by the same process shown in Scheme 1, except for using compound 7 having the α-amino group freed by partial deprotection of a protected TFB-TBOA (6). A compound of formula (2) wherein $R^1$ is a group other than hydrogen or 3-(4-trifluoromethylbenozyl)amino may also be obtained by the same process as Scheme 1 or Scheme 2. Compounds of formula (1) may be prepared in the same manner using chloroformate prepared from nitrobenzyl alcohol, for reaction with compound 2 or 7.

The compounds of the invention exhibited less than 1/300 of the inhibition exhibited by uncaged compounds against uptake of $^{14}$C-labeled glutamate by human EAAT2 constitutively expressed in MDCK (Madin-Darby Canine Kidney) cells. However, upon irradiation with a UV lamp or laser beam, they recovered their inhibitory activity in a time- or irradiation frequency-dependent manner. After using high performance liquid chromatography to examine the decomposition in aqueous solution after 1 month, almost no decomposition products were detected, thus confirming chemical stability. Consequently, the compounds of the invention are useful inhibitors whose inhibitory activity can be controlled by UV light, and they may therefore be used in analyzing transporter kinetics or the physiological significance of site-specific inhibition.

The present invention will now be explained in detail using examples, with the understanding that the invention is in no way limited to these examples.

EXAMPLE 1

Synthesis of (2S,3S)-3-benzyloxy-N-[7-(carboxymethoxy) coumarin-4-ylmethoxy]carbonylaspartate (N-CMCMC-TBOA: 5a)

To a solution of compound 1 (149 mg, 0.33 mmol) in $CH_2Cl_2$ (2 mL), TFA (1 mL) was added at 0° C. and the mixture was stirred for 1 hour at 0° C. Saturated aqueous bicarbonate solution was added and the mixture was extracted with $CHCl_3$. The extract was purified by silica gel column chromatography to obtain 92 mg of compound 2 (79% yield).

Next, to a solution of CMCM-OH (3a) (176 mg, 0.7 mmol) in THF (5 mL), trichloromethylchloroformate (0.17 mL, 1.4 mmol) was added prior to reflux for 2 hours, and then the solvent was distilled off. The residue was dissolved in $CH_2Cl_2$ (2 mL), and the resulting solution and i-$Pr_2$NEt (0.4 mL, 2.2 mmol) were added to compound 2 (85 mg, 0.24 mmol) in $CH_2Cl_2$ (2 mL), after which the mixture was stirred for 10 minutes. The solvent was distilled off and the residue was purified on a silica gel-plate to obtain 84 mg of compound 4 (51% yield).

Compound 4 (97 mg, 0.12 mmol) was then dissolved in $CH_2Cl_2$ (2 mL), and to the solution cooled in an ice bath TFA (0.5 mL) was added. The mixture was stirred for 1 hour at 0° C. and then at room temperature for 4 hours. The solvent was distilled off and the residue was purified by HPLC to obtain 25 mg of N-CMCMC-TBOA (5a) (42% yield).

$^1$H-NMR (DMSO-$d_6$) δ 4.45(d, 1H, J=12.0 Hz), 4.50 (d, 1H, J=3.6 Hz), 4.62 (dd, 1H, J=3.6, 10.0 Hz), 4.76 (d, 1H, J=12.0 Hz), 5.25 (d, 1H, J=16.4 Hz), 5.33 (d, 1H, J=16.4 Hz), 6.4 (s, 1H), 6.95 (dd, 1H, J=2.4, 9.2 Hz), 6.99 (d, 1H, J=2.4 Hz), 7.28-7.60 (m, 5H), 7.61 (d, 1H, J=9.2 Hz), 7.89 (d, 1H, J=9.2 Hz). HRMS (FAB) m/z calcd for $C_{24}H_{22}NO_{12}$(M+H)$^+$ 516.1142, Found 516.1142.

EXAMPLE 2

Synthesis of (2S,3S)-3-benzyloxy-N-[6,7-bis(carboxymethoxy)coumarin-4-ylmethoxy]carbonylaspartate (N-BCMCMC-TBOA: 5b)

The title compound 5b was obtained by the same procedure as Example 1, from compound 2 obtained in the same manner described above, except for using BCMCM-OH (3b) as the alcohol.

$^1$H-NMR (DMSO-$d_6$) δ 4.44(d, 1H, J=12.0 Hz), 4.49 (d, 1H, J=3.2 Hz), 4.61 (dd, 1H, J=3.2, 9.6 Hz), 4.75 (d, 1H, J=12.0 Hz), 4.78 (s, 2H) 4.86 (s, 2H), 5.21 (d, 1H, J=16.8 Hz), 5.31 (d, 1H, J=16.8 HZ), 6.41 (s, 1H), 7.00 (s, 1H), 7.10 (s, 1H), 7.28-7.32 (m, 5H) 7.90 (d, 1H, J=9.6 Hz). HRMS (FAB) m/z calcd for $C_{26}H_{14}NO_{15}$(M+H)$^+$ 590.1146, Found 590.1127. [α]$^{25}_D$ −9.0° (c 0.32, DMSO).

EXAMPLE 3

Synthesis of (2S,3S)—N-[6,7-bis(carboxymethoxy) coumarin-4-ylmethoxy]carbonyl-3-(4-trifluoromethylbenzoyl)aminobenzyloxyaspartate (N-BCMCMC-TFB-TBOA: 9)

To a solution of compound 6 (149 mg, 0.23 mmol) in $CH_2Cl_2$ (2 mL), TFA (1 mL) was added at 0° C. and the mixture was stirred for 1 hour at 0° C. Saturated aqueous bicarbonate solution was added, and the mixture was extracted with $CHCl_3$. The extract was purified by silica gel column chromatography to obtain 91 mg of compound 7 (74% yield).

Next, to a solution of BCMCM-OH (3b) (301 mg, 0.69 mmol) in THF (4 mL), trichloromethylchloroformate (0.17 mL, 1.4 mmol) was added prior to reflux for 2 hours, and then the solvent was distilled off. The residue was dissolved in $CH_2Cl_2$ (2 mL), and the resulting solution and i-$Pr_2$NEt (0.3 mL, 1.7 mmol) were added to a solution of compound 7 (91 mg, 0.17 mmol) in $CH_2Cl_2$ (2 mL), after which the mixture was stirred for 10 minutes. The solvent was distilled off and the residue was purified on a silica-gel plate to obtain 111 mg of compound 8 (64% yield).

Compound 8 (111 mg, 0.11 mmol) was then dissolved in $CH_2Cl_2$ (4 mL) and to the solution cooled in an ice bath TFA (0.5 mL) was added. The mixture was stirred for 1 hour at 0° C. and then at room temperature for 4 hours. The solvent was distilled off and the residue was purified by HPLC to obtain 42 mg of N-BCMCMC-TFB-TBOA (9) (49% yield).

$^1$H-NMR (DMSO-$d_6$) δ 4.46(d, 1H, J=11.6 Hz), 4.52 (d, 1H, J=3.2 Hz), 4.63 (dd, 1H, J=3.6, 9.6 Hz), 4.75 (d, 1H, J=11.6 Hz), 4.79 (s, 2H) 4.87 (s, 2H), 5.23 (d, 1H, J=16.8 Hz), 5.32 (d, 1H, J=16.8 Hz), 6.44 (s, 1H), 7.02 (s, 1H), 7.11 (s, 1H), 7.16 (d, 1H, J=7.16 Hz), 7.34 (t, 1H, J=7.2 Hz), 7.70 (d, 2H, J=6.4 Hz), 7.86-7.91 (m, 3H), 8.14 (2H, d, J=8.8 Hz). HRMS (FAB) m/z calcd for $C_{34}H_{28}F_3N_2O_{16}$ (M+H)$^+$ 777.1391, Found 777.1395. [α]$^{25}_D$ +92.7° (c 0.65, DMSO)

Evaluation of Activity

Photolysis was conducted by the known method (Takaoka, K. et al., Bioorganic & Medicinal Chemistry Letters, 13, 965-970, 2003), and the obtained samples were quantified by HPLC or a glutamate uptake assay.

Photolysis with UV Lamp

The caged inhibitor was dissolved to 100 μM in a PBS(+) solution [140 mM NaCl, 5 mM KCl, 8 mM $Na_2HPO_4$, 1.5 mM $KH_2PO_4$, 1 mM $CaCl_2$, 1 mM $MgCl_2$, pH 7.4], and a 300 μL portion of the solution was placed in a quartz cuvette with a 1 mm optical path and situated at a location at 10 cm from a UV lamp (Spectroline ENF-260C/J, product of Spectronics Co.), and then covered with a black box and irradiated with 365 nm UV rays at room temperature for 1-120 minutes. The luminous energy under these conditions was approximately 0.5 J/cm$^2$ with 10 minutes of irradiation. The irradiated sample was quantified by HPLC.

Measurement of Photolysis Rate by HPLC

Figure 1:
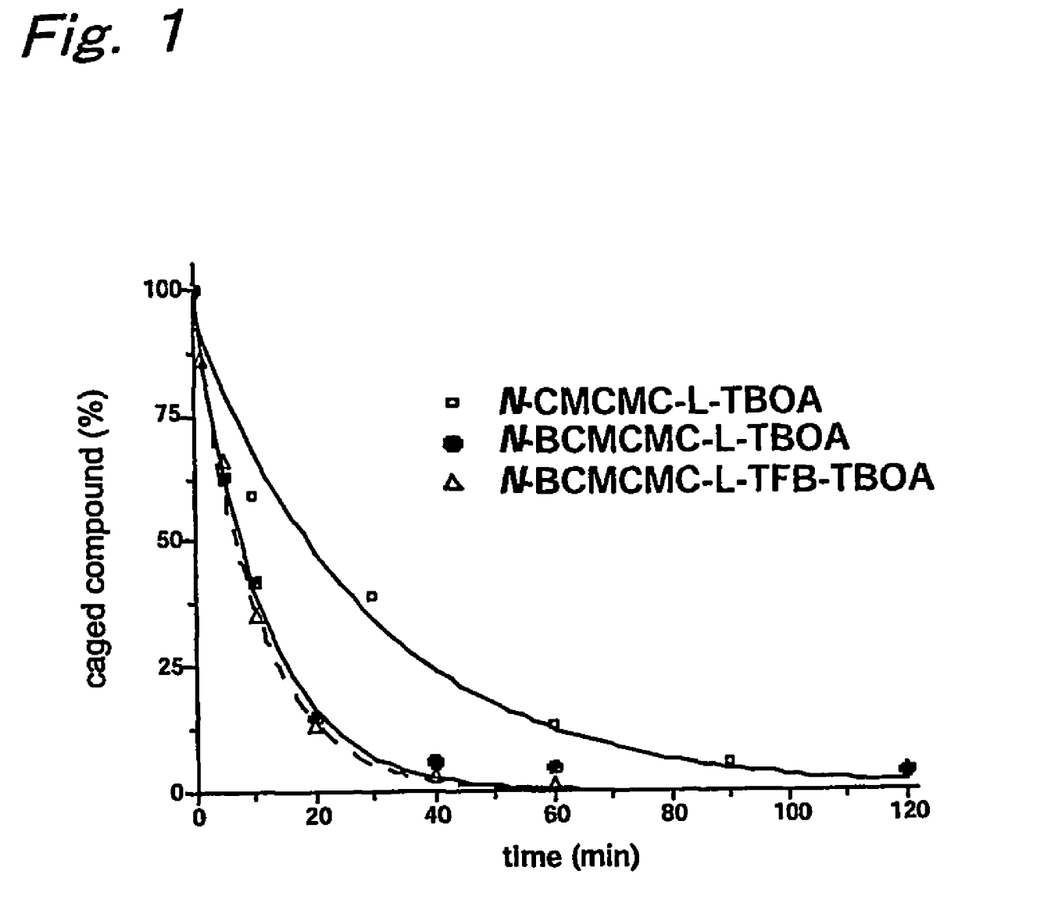
FIG. 1 is a graph showing the decay of caged compounds upon photolysis with a UV lamp.

The sample was subjected to UV irradiation for a prescribed period and then analyzed by HPLC [column: SP-120-5-ODS-AP (Daiso CO.); eluent, $CH_3CN:H_2O:TFA=32:68$:

0.1 or gradient from $CH_3CN:H_2O:TFA=32:68:0.1$ to 50:50: 0.1], and the concentration was determined from the ratio of UV absorption at 254 nm with respect to an internal substance (3',4'-dimethoxyacetophenone, 10 µM). The percentage with respect to the concentration prior to irradiation was calculated and graphed, and the half-life was determined. The half-life was 19 minutes for N-CMCMC-L-TBOA (5a), 7.8 minutes for N-BCMCMC-TBOA (5b) and 6.7 minutes for N-BCM-CMC-TFB-TBOA (9).

Photolysis with Laser Beam

The caged inhibitor was dissolved to 100 µM in a PBS(+) solution, and a 100 µL portion thereof was placed in a quartz cuvette with a 1 mm optical path and irradiated 1-128 times with 355 nm YAG laser beam [Surelite II, product of Continuum]. The period of each irradiation was approximately 8 nanoseconds, with an energy of approximately 40 mJ. The irradiated sample was provided for the following glutamate uptake assay using MDCK cells.

Glutamate Uptake Assay

Figure 2:
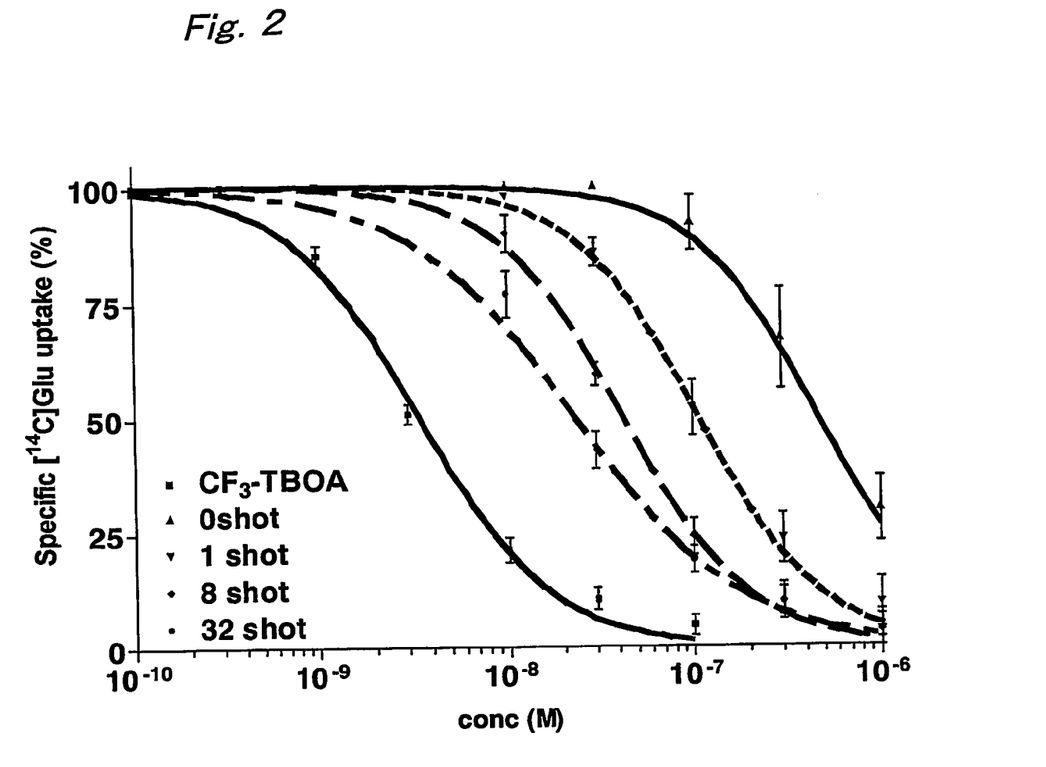
FIG. 2 is a graph showing glutamate uptake inhibitory activity of N-BCMCMC-TFB-TBOA before and after laser photoirradiation.
Figure 3:
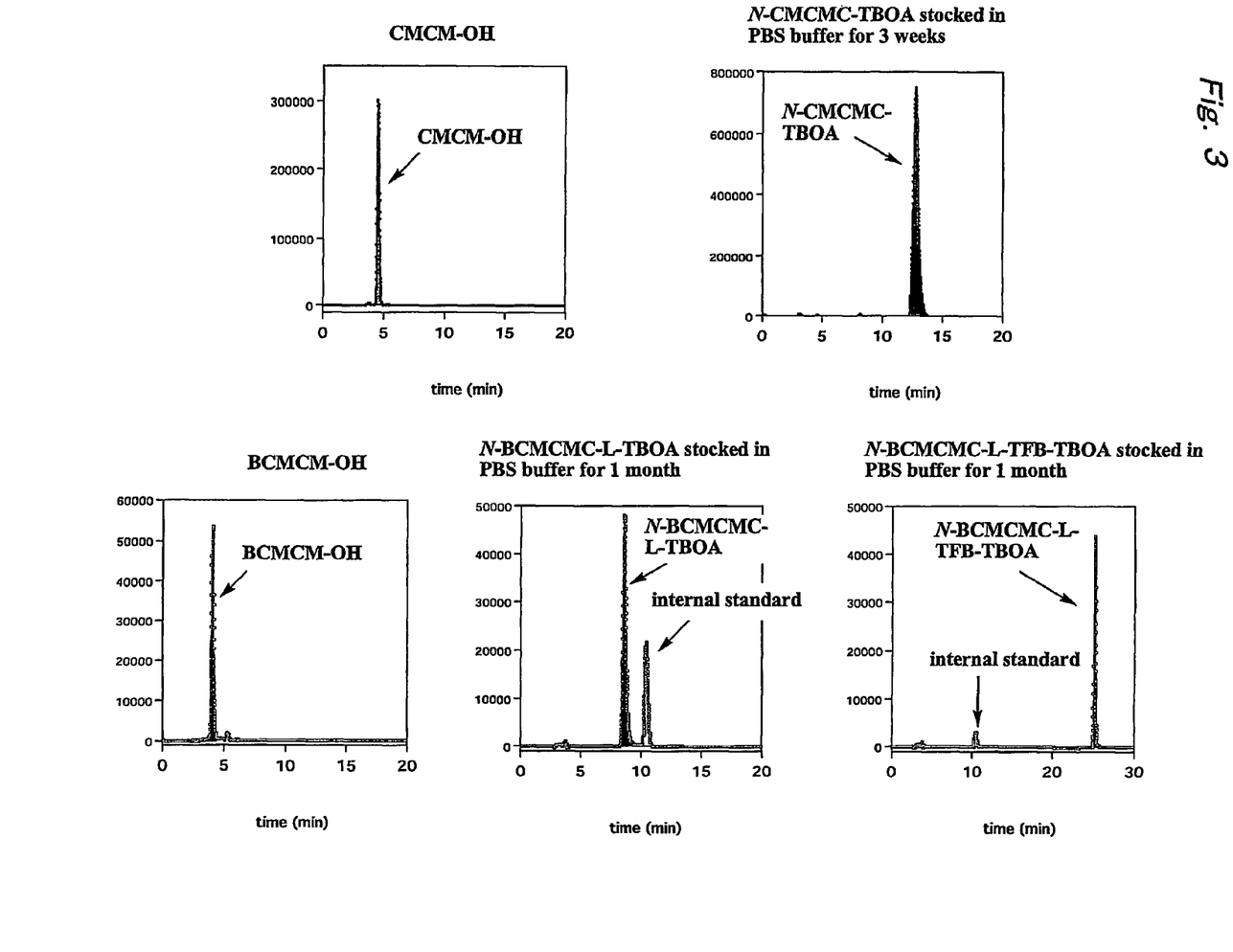
FIG. 3 shows the HPLC profile for caged compounds after storage for 1 month in aqueous solution.

The inhibitory activity against uptake of [$^{14}$C]glutamate by human EAAT2 constitutively expressed in MDCK (Madin-Darby Canine Kidney) cells was measured according to the known method (Shimamoto, K. et al., Mol. Pharmacol. 53, 195-201, 1998; Bioorg. Med. Chem. Lett. 10, 2407-2410, 2000). The glutamate uptake activity was assayed by using a liquid scintillator to measure the radiation uptake in lysed cells which had been incubated for 12 minutes after adding 1 µM L-[$^{14}$C]glutamate and a prescribed concentration of sample. The uptake was expressed on a graph as a percentage, with 100% for a sample with no compound (buffer alone) and 0% for the uptake in a sodium-free solution.

Evaluation of Stability

A PBS(+) solution (1 µM) and a DMSO solution (1 µM) containing the sample before photoirradiation were each stored for 1 month in a dark chamber at room temperature, 0° C. and −20° C., and then the decomposition products were monitored by HPLC. No decomposition products were detected in any of the samples.

The invention claimed is:

1. A compound having a substituted coumarylmethyl group connected to the nitrogen atom of the α-amino group of an L-threo-β-benzyloxylasparate or its benzene ring-substituted analog through a carbamate bond, represented by the following formula (2):

wherein $R^1$ represents hydrogen atom, amino group, straight or branched lower aliphatic acylamino group optionally substituted at the acyl group portion, alicyclic acylamino group or aromatic acylamino group optionally having a substituent on the aromatic ring, and $R^4$ and $R^5$ each represent hydrogen atom, hydroxyl group, straight or branched lower alkyloxy group optionally substituted at the alkyl portion, amino group, straight or branched lower alkyl-substituted amino group, or a halogen atom.

2. A compound according to claim 1, wherein $R^1$ in formula (2) is hydrogen atom, and $R^4$ and $R^5$ are each hydrogen atom, methoxy group or carboxymethoxy group.

3. A compound according to claim 1, wherein $R^1$ in formula (2) is 3-(4-trifluoromethylbenzoyl)amino group or 3-(4-methoxybenzoyl)amino group, and $R^4$ and $R^5$ are each methoxy group or carboxymethoxy group.

4. A method for photolysis of the compound of formula (2) as defined in claim 1, wherein the compound is subjected to light irradiation to generate the corresponding L-threo-β-benzyloxylasparate analog as a glutamate uptake inhibitor.

5. The method according to claim 4 wherein the light is UV light or laser light.

6. The method according to claim 4 or 5 wherein the light irradiation is conducted at the strength of 0.0001-100 J/cm$^2$, preferably 0.001-10 J/cm$^2$.

* * * * *